July 30, 1963 E. S. BOERNER Plant Pat. 2,270
CHRYSANTHEMUM PLANT
Filed July 19, 1962
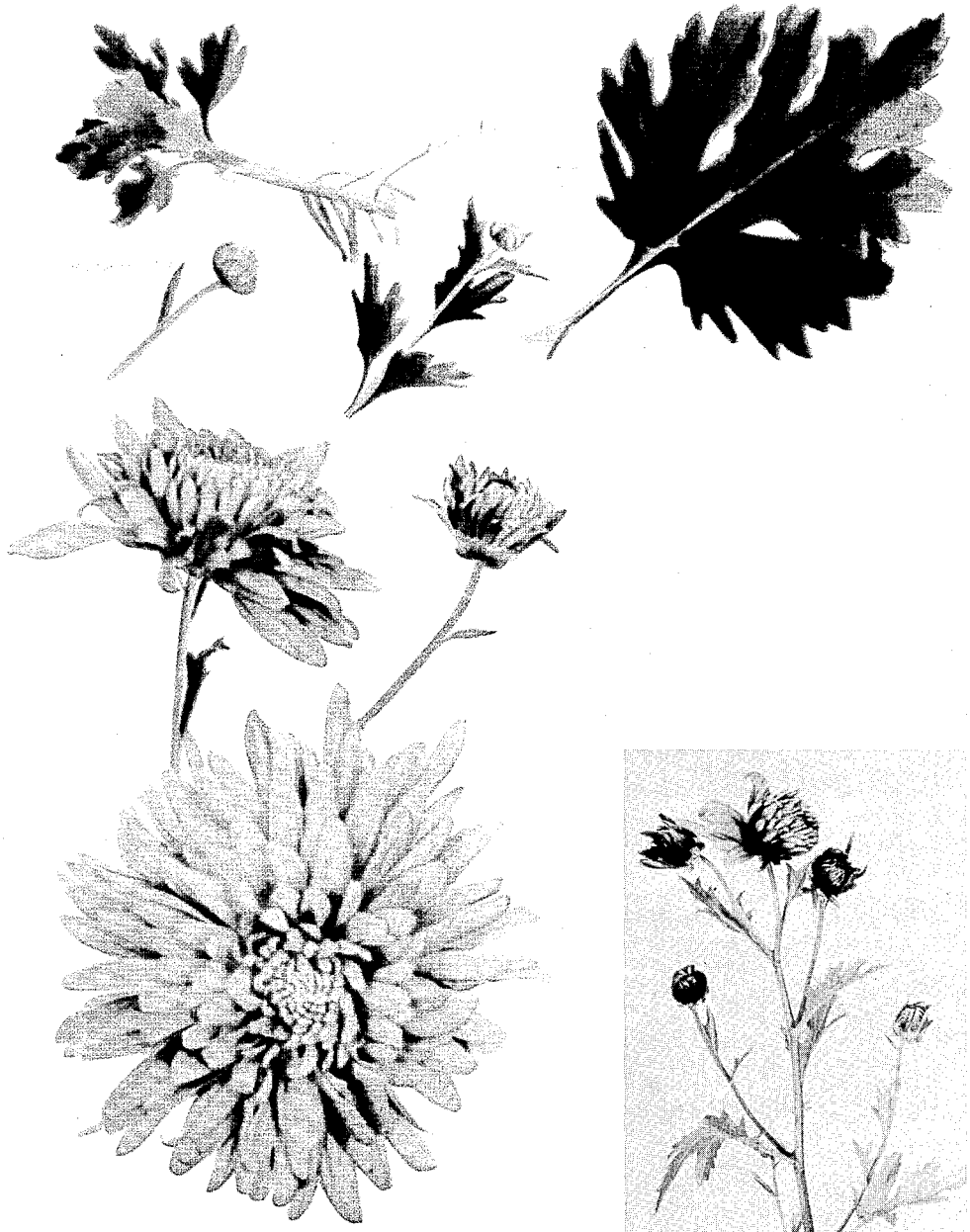
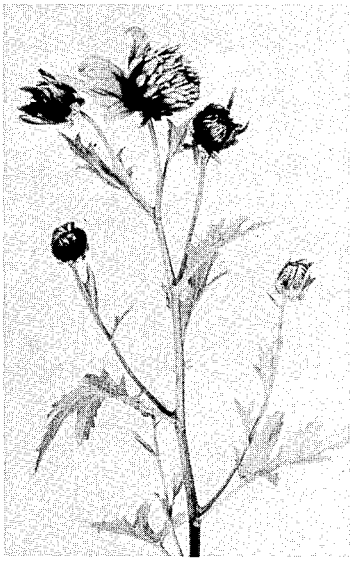
Inventor.
E. S. Boerner
By: Robb & Robb
Attorneys.

United States Patent Office

Plant Pat. 2,270
Patented July 30, 1963

2,270
CHRYSANTHEMUM PLANT

Eugene S. Boerner, Newark, N.Y., assignor to Jackson & Perkins Company, Newark, N.Y., a corporation of New York Filed July 19, 1962, Ser. No. 211,147
1 Claim. (Cl. Plt.—81)

The present invention relates to a new and distinct variety of chrysanthemum plant of the decorative class, which was originated by me by crossing an unnamed and unpatented seedling derived from a cross of "Chippewa" (unpatented) × "Tanager" (Plant Patent No. 1,129) with the variety known as "Kingbird" (Plant Patent No. 1,306).

The primary objective of this breeding was to produce a new chrysanthemum variety which combines the rich flower color of the unnamed seeding parent with the hardiness and large plant size of the parent variety "Kingbird." This objective was fully achieved, along with other desirable improvements, as evidenced by the following unique combination of characteristics which are outstanding in the new variety and which distinguish it from its parents, as well as from all other varieties of which I am aware:

(1) A hardy plant habit;
(2) A free, heavy and upright plant growth;
(3) Large plant size;
(4) Extra-large leaf size;
(5) A reflexed flower petal form in the finished flowers; and
(6) A distinctive and attractive general color tonality of the flowers corresponding to Tyrian Rose, lightly overcast with Spinel Red.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
*Seed parent.*—An unnamed seedling of "Chippewa" × "Tanager."
*Pollen parent.*—"Kingbird."

Classification: Decorative.
Growth: Very free; tall; height averages about 35 inches.
Cold resistance: Hardy in northern New York State.
Blooming period: From late September until severe frost.

*Flower*

Bud:
*Color.*—When petals first divide—Indian Lake, Plate 26. When petals begin to unfurl—Spinel Red, Plate 26. When half-blown: inside—Amaranth Purple, Plate 12, very lightly overcast with Aster Purple, Plate 12; outside—Eugenia Red, Plate 13, lightly overcast with Spinel Red, Plate 26, and with upper half of petal lightly overcast with Light Ochraceous Salmon, Plate 15.
*Peduncle.*—Color—Light Fluorite Green, Plate 32. Strength—strong.

Bloom:
*Size.*—Averages about 5 inches.
*Stem.*—Strong; stiff.
*Form.*—Decorative; outer petals reflex.
*Petalage.*—Double; oval shape.
*Color.*—Center of flower—Spinel Red, Plate 26, very lightly overcast with Tyrian Rose, Plate 12. Outer petals—Spinel Pink, Plate 26, lightly overcast with Spinel Red, Plate 26. Base of petals—Pale Greenish Yellow, Plate 5. Inside of petals—Tyrian Rose, Plate 12, lightly overcast with Spinel Red, Plate 26. Reverse of petals—Rosolane Purple, Plate 26, lightly overcast with Rose Color, Plate 26.
*Petals.*—Texture—thick. Form—oval.
*Fragrance.*—Characteristic chrysanthemum.

*Plant*

Form: Upright.
Growth: Free; heavy.
Foliage:
*Size.*—Extra large.
*Quantity.*—Normal.
*Color.*—Upper side—Forest Green, Plate 17. Reverse side—Light Bice Green, Plate 17.
*Texture.*—Leathery.

I claim:

A new and distinct variety of chrysanthemum plant of the decorative class, substantially as herein shown and described, characterized particularly as to novelty by the unique combination of a hardy plant habit, a free, heavy and upright habit of plant growth, large plant size, extra-large leaf size, a reflexed flower petal form in the finished flowers, and a distinctive and attractive general color tonality of the flowers corresponding to Tyrian Rose, lightly overcast with Spinel Red.

No references cited.